(12) United States Patent
Eggink et al.

(10) Patent No.: US 7,811,995 B2
(45) Date of Patent: Oct. 12, 2010

(54) THERAPEUTIC AND DIAGNOSTIC PEPTIDES

(75) Inventors: Laura L. Eggink, Scottsdale, AZ (US); Kenneth J. Hoober, Phoenix, AZ (US)

(73) Assignee: Susavion Biosciences, Inc., Temple, AZ (US)

( * ) Notice: Subject to any disclaimer, the term of this patent is extended or adjusted under 35 U.S.C. 154(b) by 0 days.

(21) Appl. No.: 11/955,226

(22) Filed: Dec. 12, 2007

(65) Prior Publication Data

US 2008/0292650 A1    Nov. 27, 2008

Related U.S. Application Data

(60) Provisional application No. 60/869,865, filed on Dec. 13, 2006, provisional application No. 60/974,056, filed on Sep. 20, 2007.

(51) Int. Cl.
*A61K 38/08* (2006.01)
*C07K 7/06* (2006.01)

(52) U.S. Cl. ............... 514/16; 514/17; 530/328; 530/330

(58) Field of Classification Search ............ None
See application file for complete search history.

(56) References Cited

U.S. PATENT DOCUMENTS

| | | | |
|---|---|---|---|
| 5,641,747 A | | 6/1997 | Popoff et al. |
| 5,753,481 A * | | 5/1998 | Niwa et al. ............ 435/190 |
| 6,193,981 B1 | | 2/2001 | Goldstein |
| 6,498,020 B1 * | | 12/2002 | Walker et al. ............ 435/69.1 |
| 6,551,795 B1 | | 4/2003 | Rubenfield et al. |
| 2004/0123343 A1 * | | 6/2004 | La Rosa et al. ............ 800/278 |
| 2004/0248192 A1 | | 12/2004 | Marchalonis et al. |
| 2005/0063937 A1 | | 3/2005 | Li et al. |
| 2006/0078535 A1 * | | 4/2006 | Livant ............ 424/78.27 |
| 2006/0148093 A1 | | 7/2006 | Gygi et al. |
| 2006/0189538 A1 | | 8/2006 | Secombes et al. |
| 2006/0269519 A1 | | 11/2006 | Chen et al. |
| 2007/0003542 A1 | | 1/2007 | Zimmerman et al. |

(Continued)

FOREIGN PATENT DOCUMENTS

CA    2290722 A1 *    6/2001

(Continued)

OTHER PUBLICATIONS

PCT/US2007/087425 International Search Report dated Aug. 5, 2008.

(Continued)

*Primary Examiner*—Jeffrey E Russel
(74) *Attorney, Agent, or Firm*—Fennemore Craig, P.C.

(57) ABSTRACT

This invention generally relates to peptides useful for medical diagnosis and treatment of pathogenic disorders. More specifically, the invention relates to immunostimulatory peptides which can stimulate the production of therapeutically beneficial cytokines and, in combination with antibodies against human pathogens such as the immunodeficiency virus (HIV), inhibit replication of such pathogens. The peptides interact synergistically with pathogen-directed antibodies without producing or sustaining serious side-effects such as inflammation, and provide the potential for treatment modalities that are non-specific with respect to pathogen and cell type. Therefore, the peptides of the present invention have wide applicability with respect to medical treatment of pathogen-mediated infections, and the potential to enhance well-being.

26 Claims, 4 Drawing Sheets

U.S. PATENT DOCUMENTS

| | | | |
|---|---|---|---|
| 2008/0102076 | A1 | 5/2008 | Eggink et al. |
| 2009/0041793 | A1 | 2/2009 | Eggink et al. |

FOREIGN PATENT DOCUMENTS

| | | |
|---|---|---|
| WO | 96/40903 | 12/1996 |
| WO | 00/31130 | 6/2000 |
| WO | 02/058589 | 8/2002 |
| WO | 03/091275 | 11/2003 |
| WO | 2004/011650 | 5/2004 |
| WO | 2005/087793 | 9/2005 |
| WO | 2006/063028 | 6/2006 |

OTHER PUBLICATIONS

Sarig, et al.; "Telomeric and Tetraplex DNA Binding Properties of qTBP42: A Homoloque of the CArG Box Binding Protein CBF-A"; Biochemical and Biophysical Research Communications 1997, vol. 237, No. 3, pp. 617-623.

J. Cohen, "Hope on New AIDS Drugs, but Breast-Feeding Strategy Backfires," Science (2007), vol. 315, pp. 1357.

J. Stover et al., "The Global Impact of Scaling up HIV/AIDS Prevention Programs in Low- and Middle-Income Countries," Science (2006) vol. 311, pp. 1474-1476.

G. Fätkenheuer et al., "Efficacy of Short-Term Monotherapy with Maraviroc, a New CRC5 Antagonist, in Patients Infected with HIV 1," Nature Med (2005), vol. 11, pp. 1170-1172.

Glaxosmithkline, (2005a) Study of Chemokine Coreceptor 5 (CCR5) Antagonist GW873140 in R5-Tropic Treatment-Experienced HIV Infected Subjects, ClinicalTrials.gov (Sep. 13, 2005) Identifier: NCT00197145S, (Terminated in 2005).

Glaxosmithkline, (2005b) "GlaxoSmithKline Halts Trials of Experimental CCR5 Inhibitor Aplaviroc in Treatment-naïve HIV Patients Due to Concerns about Liver Toxicity," Statement to HIV Patient Community: Information from GlaxoSmithKline on Changes to Studies of Investigational CCR5 Entry Inhibitor Aplaviroc (GW873140) (Sep. 15, 2005), pp. 1-2.

P.W. Latham, "Therapeutic Peptides Revisited," Nature Biotech (1999), vol. 17, pp. 755-757.

Supplementary European Search Report for European application No. 07871699.0 dated May 17, 2010 (8 sheets).

International Search Report for WO/2005/087793 dated Apr. 5, 2006 (6 sheets).

Written Opinion of the International Searching Authority for WO/2005/087793 dated Apr. 5, 2006 (7 sheets).

International Search Report for WO/2006/063028 dated Nov. 16, 2006 (6 sheets).

Written Opinion of the International Searching Authority for WO/2006/063028 dated Nov. 16, 2006 (9 sheets).

Written Opinion of the International Searching Authority for WO/2008/076815 dated Jul. 29, 2008 (6 sheets).

Written Opinion of the International Searching Authority for WO/2008/076824 dated Aug. 5, 2008 (6 sheets).

Ciesielski et al., "Cellular antitumor immune response to a branched lysine multiple antigenic peptide containing epitopes of a common tumor-specific antigen in a rat glioma model", Cancer Immunol Immunother, 54:107-119 (2005).

Eggink et al., "A biologically active peptide mimetic of N-acetylgalactosamine/galactose", BMC Research Notes, 2:23 (2009).

Nicolaus, "Symbiotic Approach to Drug Design", Decision Making in Drug Research, pp. 173-186 (Jan. 1, 1983).

Olszewska et al., "Protection against Measles Virus-Induced Encephalitis by Anti-mimotope Antibodies: The Role of Antibody Affinity", Virology, 272(1):98-105 (Jun. 20, 2000).

Chargelegue et al., "A Peptide Mimic of a Protective Epitope of Respiratory Syncytial Virus Selected from a Combinatorial Library Induces Virus-Neutralizing Antibodies and Reduces Viral Load In Vivo", Journal of Virology, 72(3):2040-2046 (Mar. 1998).

Chersi et al., "Specificities of rabbit antisera to multiple antigen (MAP) peptides", Journal of Biosciences, 50(9-10):735-738 (Sep. 1, 1995) ABSTRACT ONLY.

Manki et al., "Vaccination with Multiple Antigen Peptide as Rejection Antigen Peptide in Murine Leukemia", Cancer Research, 58:1960-1964 (May 1, 1998).

Nicolaus, "Symbiotic Approach to Drug Design", Decision Making in Drug Research, pp. 173-186 (Jan. 1, 1983).

European Search Report for European patent application No. 07869233.2 dated May 11, 2010.

* cited by examiner

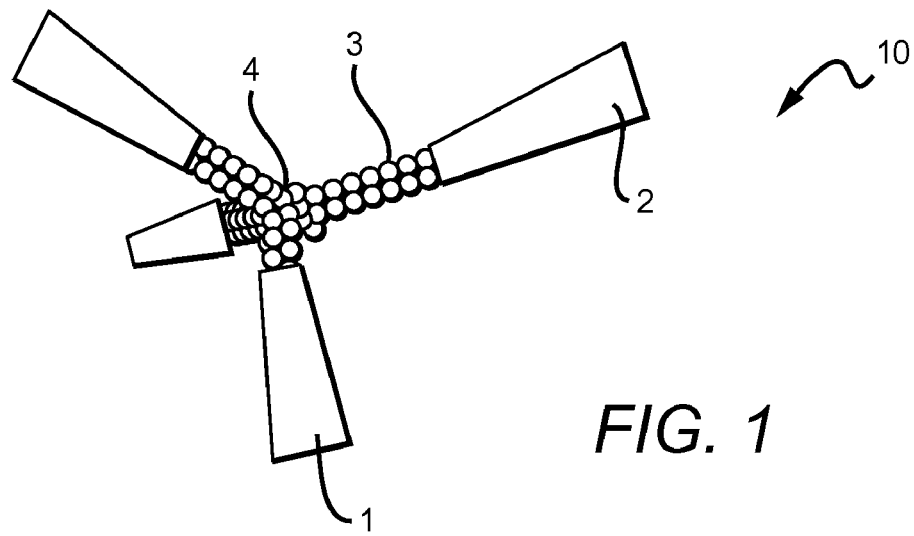
FIG. 1
FIG. 2A
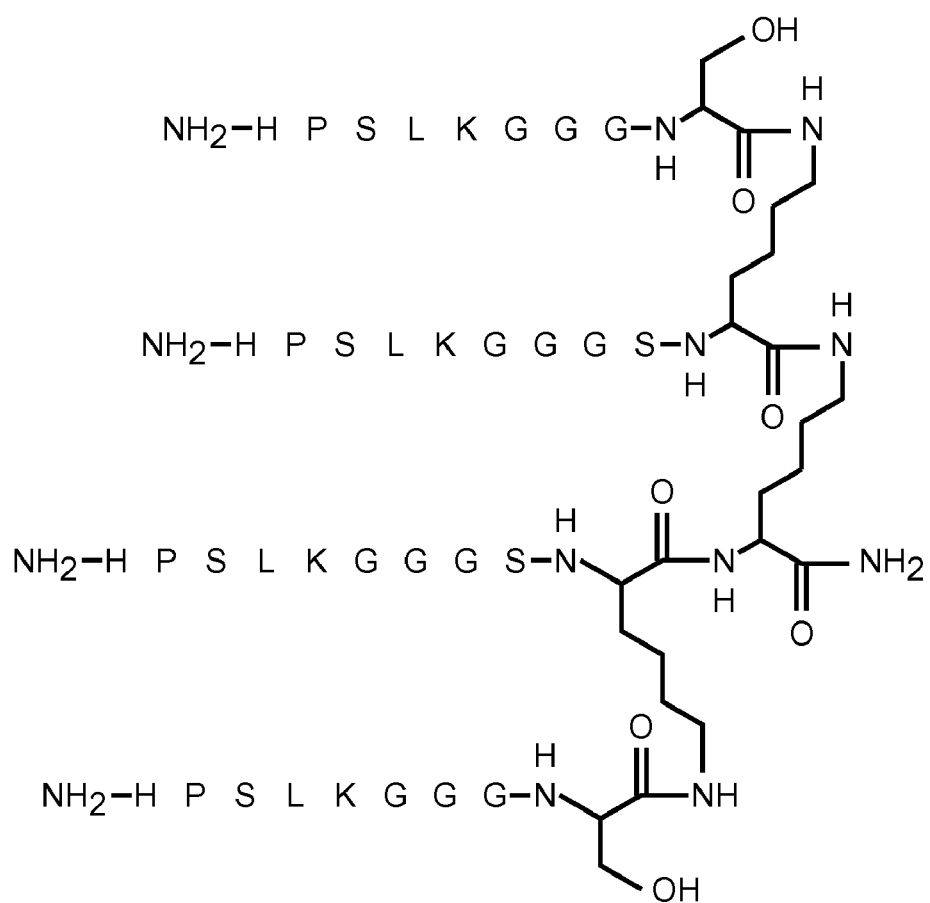

THERAPEUTIC AND DIAGNOSTIC PEPTIDES

CROSS REFERENCE TO RELATED APPLICATIONS

This application claims priority to the earlier provisional application entitled "Induction of Cytokine Defense Against HIV Infections," Ser. No. 60/869,865, filed Dec. 13, 2006 and to the earlier provisional application entitled "Therapeutic and Diagnostic Peptides," Ser. No. 60/974,056, filed Sep. 20, 2007, the disclosures of which are hereby incorporated herein by reference.

BACKGROUND

1. Technical Field

The present invention relates generally to the use of synthetic peptides for treating human disorders and diseases and, in particular, to peptides and methods for the prevention, diagnosis and treatment of infections, cell proliferative diseases and immunosuppressive disorders.

2. State of the Art

Approximately 40 million people are infected with HIV world-wide and 10% of these individuals will die each year from AIDS. In addition, the annual number of new infections is estimated to be 5 million and rising. The cost of treating this disease is enormous, and varies from $2,500 per patient in Brazil to over $10,000 per patient per year in developed countries. Cost of prevention is estimated at more than $120 billion over the next 10 years, although the long-term benefit from prevention would dramatically reduce future costs for treatment and care. The bulk of the cost of current treatment is for anti-retroviral drugs, which are remarkably effective but often lead to resistance. Furthermore, long-term control of the infection, most likely by management as a low-grade, chronic disease, increases the cost burden beyond that which can be afforded in low- and middle-income countries.

HIV-1 enters into cells by first attaching to one or more receptors on a cell, thereby inducing conformational and/or structural changes that allow insertion of the viral genome into the cell. Once inside the cell, the viral genome is then free to replicate. The primary therapies against HIV infections are anti-retroviral drugs that inhibit viral replication after entry into the cell. The most commonly used are nucleoside reverse transcriptase inhibitors, non-nucleoside reverse transcriptase inhibitors, and protease inhibitors that block enzymatic processing of viral products. These drugs effectively inhibit replication of the virus inside an infected cell and reduce viral load in the blood to undetectable levels.

Another therapeutic approach uses fusion inhibitors, including proteins (e.g. monoclonal antibodies), peptides and small molecule agents (e.g. drugs), some of which act on the outside of the cell to prevent HIV from fusing with and infecting it. If HIV cannot penetrate the host cell membrane and infect the cell, then HIV cannot replicate. Fusion inhibitors effectively block infection by HIV-1 and significantly reduce the systemic viral load. Vaccines that elicit antibodies that inhibit such fusion are of interest in this regard, and several pharmaceutical companies are working to achieve this goal.

Combinations of small molecular weight drugs, however, achieve undetectable levels of HIV virus in only about 50 to 60% of treated patients. In addition, the development of treatments that involve antibodies is generally costly and requires considerable medical infrastructure. Furthermore, although the development of prophylactic treatments such as vaccines is an important effort, particularly for susceptible target populations, protocols must also be developed for those already infected.

In contrast to therapeutic approaches aimed at prevention or control of the disease by directly inhibiting a step in the viral replication cycle, as described above, reactivation of patients' immune system is an alternative therapy that holds promise for restoring health and productivity to an infected patient in a practical, cost-effective manner. As a result, an intense interest in immunotherapy, as indicated by the development of cytokine treatments for example, is leading to products that can stimulate or inhibit the immune system. One developmental cytokine/immunomodulator project for the treatment of HIV/AIDS has, for example, identified two key peptides derived from Thymus Nuclear Protein (TNP) technology (Viral Genetics, Inc., Azusa, Calif.), These peptides occur naturally in a variety of mammals, including humans.

The role of cytokines in the inhibition of HIV infectivity, particularly interleukin-16 (IL-16), interleukin-8 (IL-8) and RANTES (Regulated upon Activation, Normal T-cell Expressed, and Secreted; also known as CCL5), is very important. HIV-1 enters cells by first binding to two key molecular components on the cell surface, the protein CD4 and co-receptors CCR5 or CXCR4. CD4(−) cells are therefore insensitive to HIV, and genetic inactivation of CCR5 correlates strongly with resistance to HIV-1 infection. Cytokines such as IL-16, IL-8 and RANTES, which have overlapping and complementary functions, can act to attenuate viral infection by competing with viral binding and by interfering with viral entry into cells by down-regulating the receptors required for entry. Other cytokines such as interferons (e.g. IF-α and IF-γ) act to reduce viral load by stimulating antibody-mediated phagocytosis.

Interleukins (IL's) and interferons (IF's) are potent cellular stimulants that are released from a variety of cells in response to insult or injury. Consequently, these proteins have attracted intense interest as therapeutic agents. However, similar to general stimulants such as lipopolysaccharide (LPS), IL's and IF's induce release of inflammatory cytokines and thus, when given at higher than normal concentrations during therapy, have substantial adverse effects resulting from inflammation which can be life-threatening and may require inpatient treatment facilities. Similarly, levels of TNF-α, IL-1β and IL-6 are directly correlated with the probability of death in humans. Moreover, production of recombinant IL's and IF's and their application are very costly, and even lower-dosage immunostimulant treatments developed for out-patient use have lower success rates and are not suitable in some situations such as, for example, to extend remission from cancer therapy or control a disease such as HIV at a chronic level.

In general, a stimulant of IL-8 and IL-16 release appears to be particularly suited for a role in enhancing host defense. Selective release of IL-8 by monocytes is possible without the release of inflammatory cytokines such as IL-1β and IL-6. However, a potentially adverse effect of IL-8 production is the enhanced recruitment of neutrophils to inflamed endothelial cells and subsequent release of cytotoxic factors which cause cell/tissue damage, in addition to the continued production of IL-8 by adjacent (non-inflamed) enthothelial cells. The consequence is a vicious cycle of recruitment of neutrophils in response to IL-8, damage to tissues, and more production of IL-8, although higher concentrations of IL-8 can be beneficial when they lead to internalization of receptors and de-sensitization of the cells. Therefore, exogenous therapeutic agents such as large, intact cytokine molecules are not well suited for general therapeutic use.

Information relevant to attempts to address one or more of these problems can be found in the following references: U.S. Patent Publication No. 2007/0003542; U.S. Patent Publication No. 2006/0269519; U.S. Patent Publication No. 2004/0248192; P. W. Latham, 1999; Fatkenheuer et al., 2005; Stover et al., 2006; Cohen, 2007; GlaxoSmithKline, 2005a and GlaxoSmithKline, 2005b. However, each one of these references suffers from one or more of the following disadvantages:

1. the size or composition of the agent provides significant challenges to cost-effective synthesis and purification;
2. the agent is specific for particular pathogen and/or cell type, rendering them unsuitable for general therapeutic use;
3. treatment with the agent induces clinically deleterious side effects that can be life-threatening, such as inflammation or hepatotoxicity, and require inpatient treatment facilities;
4. termination of treatment is followed soon thereafter by an increased systemic viral load;
5. long term exposure to agent often leads to treatment-resistant pathogens;
6. lower-dosage treatments developed for out-patient use have lower success rates and are not suitable in some situations;
7. treatment is ineffective, impractical, or cost-prohibitive for a large proportion of patients;
8. development of therapeutic antibodies require considerable medical infrastructure;
9. treatment such as vaccines may be appropriate to prevent infection but not to treat those already infected;
10. no beneficial synergy between the immunogenic response induced and the effects of other endogenous immunoregulators;
11. agent inhibits the release of inhibitory cytokines that suppress release of beneficial cytokines, an indirect treatment; and
12. agent acts to restore baseline cytokine levels to balance responses of the immune system rather than promoting activation of phagocytes.

Many of these therapeutic protocols also become ineffective with time because mutation of the pathogen allows it to escape the treatment. Moreover, any immunosuppression that accompanies the disease attenuates the ability of the innate immune system to respond to antigenic changes and thereby keep the infection under control. However, even though the virus may mutate at one or a few sites and thereby escape the neutralizing activity of antibodies, endogenously produced antibodies are usually polyclonal and may still bind the virus.

The immune system in individuals infected with a pathogenic agent such as HIV initiates a defense response by production of antibodies. The presence of anti-HIV antibodies is often used as a diagnostic test for infection. During the course of the disease, the antibody level remains high whereas the ability to maintain a minimal viral load gradually weakens as the population of CD4+ T cells declines. The cellular components of the innate immune response then become absent or quiescent. When the immune defense mechanisms reach a sufficiently low level, viral replication is not held in check and rapidly leads to a final stage of the disease, designated AIDS. However, even at this late stage, patients can be rescued from death by aggressive anti-retroviral therapy. Therefore, an agent that reactivates cells of the immune system, in particular phagocytes, will likely also restore an immune defense against progression of the disease.

In light of the available treatments for infections such as HIV induced AIDS, there are large numbers of people worldwide that need alternative, practical, cost-effective, non-specific therapies that directly bolster a patient's immune system during the course of the disease without causing deleterious side effects. Ideally, such therapies should also be effective against other types of pathogens.

Therapeutic agents that activate/reactive the immune system show particular promise in this regard, including cytokines and immunomodulators, although therapies based on exogenous agents such as large, intact cytokine molecules are not generally well suited for therapeutic use. Peptides, however, are often much more suitable therapeutic agents than large polypeptides or proteins. Peptides can, for example, be designed to induce one or more particular desired effects in vitro or in vivo, often without concomitantly inducing deleterious effects, and can usually be synthesized in a cost effective manner.

SUMMARY

The present invention generally relates to peptides and treatments that mitigate or nullify the effects of pathogenic agents by stimulating the production of therapeutically beneficial cytokines. More particularly, the invention relates to immunostimulatory peptides which, when used in combination with antibodies against human pathogens such as the immunodeficiency virus (HIV), effectively eliminate such pathogens. The peptides may, in combination with antibodies, be used as microbicides and may also be used to treat cell proliferative diseases and/or immunosuppressive disorders.

The peptides of the present invention can work synergistically with pathogen-directed antibodies by stimulating the phagocytic cells that digest the pathogen after antibody-mediated phagocytosis. In addition, the peptides and treatments of the present invention do not produce or sustain serious side-effects such as inflammation.

Therefore, the peptides and treatments of the present invention provide alternative, practical, cost-effective treatments which can be non-specific with respect to pathogen and cell type, and therefore have wide applicability for medical treatment of pathogen-mediated infections.

In one specific embodiment, the therapeutic peptide includes at least one core sequence having at least four amino acid residues, the core sequence being selected from the group consisting of: $X_m$-P-$X_n$-S-$X_p$; $X_m$-G-$X_n$-S-$X_p$; $X_m$-P-$X_n$-T-$X_p$; and $X_m$-G-$X_n$-T-$X_p$, where P is proline, S is serine, G is glycine, T is threonine, X is a naturally occurring L-amino acid, and m, n, and p are integers whose sum is at least 2, and fragments or derivatives thereof which are also therapeutically viable. In one aspect, the peptide contains 4 to 8 amino acids and the sum of the integers m, n, and p is within the range of 2 to 6. In another aspect, the peptide is immunostimulatory and at the least one core sequence is selected from the group consisting of VGGGS (SEQ ID NO:1), PSSNA (SEQ ID NO:2), HPSLK (SEQ ID NO:3), HPSLG (SEQ ID NO:4), HPSLL (SEQ ID NO:5), HPSLA (SEQ ID NO:6), NPSHPLSG (SEQ ID NO:7), and NPSHPSLG (SEQ ID NO:8).

Another embodiment of the present invention is an immunostimulatory composition that includes at least one therapeutic peptide having at least one core sequence. In one aspect, the peptide can be part of a linear or branched peptide construct. In another aspect, one to four peptides may be present in the construct. In yet another aspect, the construct includes a linker sequence such as GGGS (SEQ ID NO:9).

Yet another embodiment of the invention is a method for treating a medical condition that includes administering a composition containing at least one therapeutic peptide having a core sequence. In one aspect, treatment can be achieved without causing one or more deleterious side effects. In another aspect, the method can be used for treating one or more microbial infections, cell proliferative diseases and/or immunosuppressive disorders. In a further aspect, the medical condition being treated can be a viral infection such as a human immunodeficiency virus infection and/or a cell proliferative disease such as a cancer. In yet another aspect, the condition is a microbial infection and the composition is a microbicide.

In another aspect of the method for treating a medical condition, administration of the composition stimulates the production of at least one therapeutically beneficial cytokine and the activity of at least one pathogen directed antibody. In a further aspect, the composition can stimulate the activity of at least one pathogen directed antibody by interacting synergistically with and/or activating at least one phagocytic cell. In another aspect, the pathogen directed antibody can be an anti-viral, anti-cancer, anti-bacterial, anti-protozoal, anti-fungal antibody, or combination thereof. In yet another aspect, the method may include the release of a specific pattern of cytokine molecules in a subject and/or stimulation of the immune system of the subject. In a further aspect, the composition can be administered to the subject using one or more approaches such as by injection, topically and orally.

A further embodiment of the invention is a diagnostic method that includes incubating one or more portions of at least one test sample with at least one composition containing at least one peptide having a core sequence and, optionally, incubating at least one portion of at least one test sample in the absence of at least one composition. In one aspect, the method is used for evaluating the capacity of an immune system to respond to at least one pathogen directed antibody. In another aspect, the method is used for evaluating the capacity of one or more components of the immune system to neutralize replication of at least one virus. In yet another aspect, the virus is a human immunodeficiency virus. In a further aspect, the method can be used for evaluating the capacity of an immune system to stimulate the activity of at least one phagocytic cell.

BRIEF DESCRIPTION OF THE DRAWINGS

FIG. 1 illustrates a working model of the molecular structure of one embodiment of the invention, a multivalent immunoregulatory peptide construct containing four peptides according to the invention, each of which is linked to a central framework via linker sequence;

FIG. 2A illustrates the chemical structure of a peptide construct according to one embodiment of the invention, the construct Peptide 6B (SynGia™6B) containing four copies of the core sequence HPSLK (SEQ ID NO:3) linked to a branched central framework structure;

DETAILED DESCRIPTION

Figure 2B:
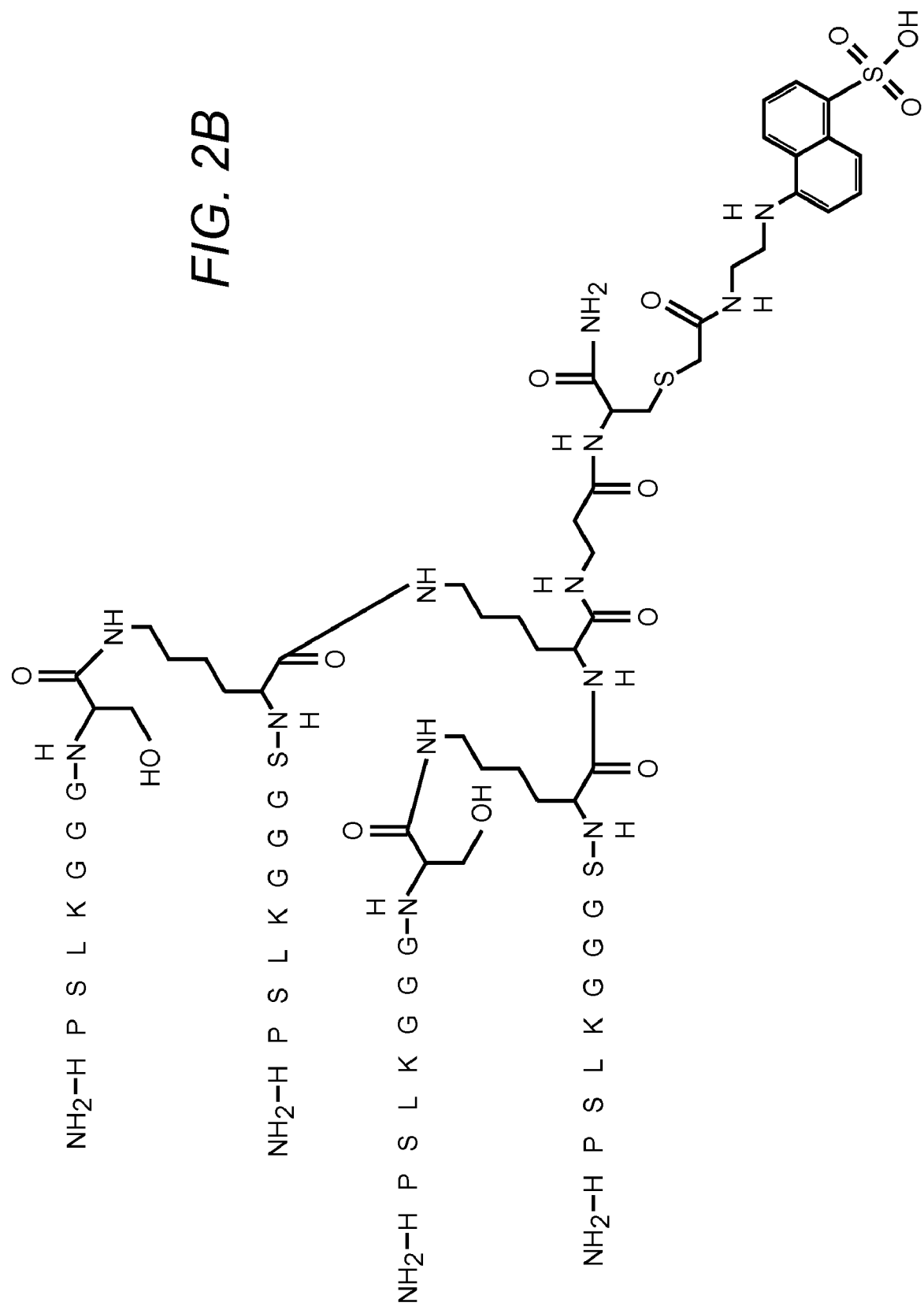
FIG. 2B illustrates the chemical structure of a peptide construct according to one embodiment of the invention, the construct as shown in FIG. 2A to which a dansyl tag has been added.
Figure 3:
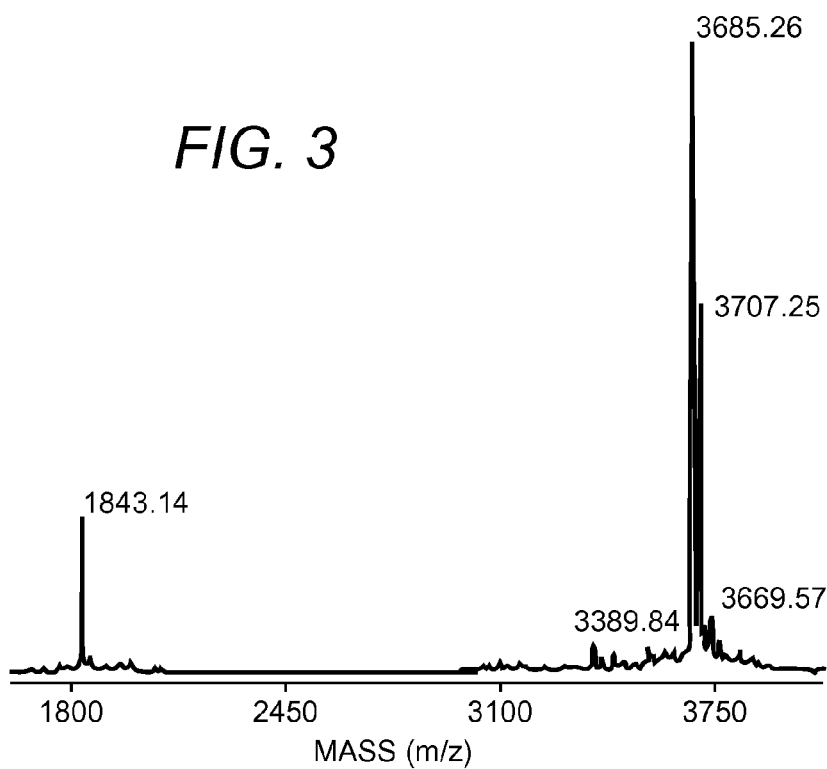
FIG. 3 is a mass spectrum of the peptide construct illustrated in FIG. 2A.

In order to provide a non-specific therapeutic agent with a relatively broad front, an agent that induces beneficial cytokine production should work in concert with the phagocytic activity of immune cells. The peptides of the present invention can accomplish this goal by concomitantly inducing the release of beneficial cytokines and stimulating the immune system, including phagocytes, to respond to the presence of pathogen-directed antibodies. Treatment with the peptides of the present invention should therefore induce activation of cells of the immune system in vivo and provide a sustained endogenous elevation of beneficial cytokines, in contrast to the rapid disappearance of these proteins when given exogenously.

An inducer of the endogenous production of specifically IL-2, IL-8, IL-15 and IL-16 should sustain an elevated level of beneficial cytokines that enhances the overall defense mechanism of the body without reaching concentrations that cause toxic side effects such as inflammation. Furthermore, selective cross-linking of cell-surface receptors by a multivalent structure incorporating at least one peptide of the present invention should act to attenuate viral infection by interfering with viral entry into cells and to stimulate activity of phagocytic cells to eliminate viral particles, thus enhancing treatment by minimizing or preventing further infection by active pathogens.

The following description presents embodiments of the invention representing various modes contemplated for practicing the invention. This description is not to be taken in a limiting sense but is made merely for the purpose of describing the general principles of the invention, whose scope is defined by the appended claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable processes and materials are described below. All publications, patent applications, patents, and other references mentioned herein are incorporated by reference in their entirety. In case of conflict, the present specification, including definitions, will control. In addition, the materials, processes, and examples are illustrative only and not intended to be limiting.

The following definitions refer to the particular embodiments described herein and are not to be taken as limiting; the invention includes equivalents for other undescribed embodiments.

As used herein, the term "construct" when referring to a peptide is intended to mean a framework supporting one or more peptides, including without limitation a tri-lysine central framework supporting four identical peptide sequences within the same structure.

As used herein, the term "core sequence" is intended to mean a peptide having at least one of the following amino acid sequences:

$X_m$-P-$X_n$-S-$X_p$;
$X_m$-G-$X_n$-S-$X_p$;
$X_m$-P-$X_n$-T-$X_p$; and
$X_m$-G-$X_n$-T-$X_p$, wherein P is proline, S is serine, G is glycine, T is threonine, X is a naturally occurring L-amino acid, and m, n, and p are integers greater than or equal to zero. A core peptide sequence, and fragments or derivatives thereof, therefore contains at least one of the following pairs of amino acids: P and S (P/S), G and S (G/S), P and T (P/T), or G and T (G/T).

As used herein, the term "cytokine" is intended to a messenger molecule that controls the activity of cells, including without limitation cells of the immune system. Cytokines can control cell activity through several mechanisms, including without limitation by allowing cells to communicate and alter one another's function. Nonlimiting examples of cytokines include immunoregulatory proteins such as interleukins and interferons, which are secreted by cells of the immune system and can affect the immune response.

As used herein, the term "deleterious inflammation" is intended to mean clinically manifested inflammation which is deleterious with respect to treatment.

As used herein, the term "effective dose" is intended to mean an amount of a peptide that, when administered to a subject, is sufficient to achieve a desirable, comprehensive, or otherwise satisfactory therapeutic response, including without limitation an optimal response and a maximal or near maximal response.

As used herein, the term "immunomodulator" or "immunomodulatory" when referring to a substance or agent is intended to mean a substance or agent that affects the functioning of the immune system.

As used herein, the term "immunostimulatory" is intended to mean relating to or producing an immune response, including without limitation immunogenic substances or agents which produce an immune response.

As used herein, the term "immunoregulatory" is intended to mean of or relating to the regulation of the immune system, including without limitation immunoregulatory T cells.

As used herein, the term "infection" is intended to mean a clinically manifested state or disease produced by the establishment of an infective agent either in or on a suitable subject or host.

As used herein, the term "stimulant" is intended to mean an agent that produces a temporary increase of the functional activity or efficiency of an organism or any of its parts, including without limitation a synthetic drug or naturally occurring substance such as adrenaline.

As used herein, the term "stimulate" or "stimulating" is intended to mean to excite to activity or growth, or to greater activity.

As used herein, the term "subject" is intended to mean one that is acted on during the course of treatment, including without limitation a human or non-human individual awaiting or under medical care and treatment.

As used herein, the term "therapeutic" when referring to a substance or treatment is intended to mean a substance or treatment concerned with providing or assisting in a cure for, or ameliorating the symptoms of, a bodily dysfunction such as that caused by disease or injury.

The present invention generally relates to a family of synthetic peptides capable of inducing the release of beneficial cytokines and also stimulating the immune system to respond to the presence of pathogen-directed antibodies.

FIG. 1 illustrates a working model of the molecular structure of one embodiment of a multivalent immunoregulatory peptide construct 10 according to the invention. The construct 10 can be synthesized with either two, three, four, eight or more arms 1, using the same core peptide sequence 2 on all four arms or with two or more different sequences. The length of the spacer 3 between the central framework 4 of the construct and the core peptide sequence 2 determines the length of the arm 1. The arms 1 illustrated in FIG. 1, for example, can be about 3±0.5 nm in length depending on conformation, or approximately 7 nm across the molecule. Cell-surface domains of known receptor proteins are correspondingly about 3 to 4 nm in diameter. This distance can be adjusted by increasing or decreasing the length of the linker. Therefore, cross-linking of receptors can be achieved with such an embodiment. The multidimensional nature of the structure illustrated in FIG. 1 was obtained using standard molecular modeling techniques.

EXAMPLES

Example 1

Peptide Design and Synthesis

A screen of peptide sequences identified one set of sequences of interest. The corresponding peptides were synthesized by solid-phase methods using standard Fmoc side chain protection. Branched peptides were constructed on a central tri-lysine framework, which allows four identical sequences within the same structure. A linker sequence, (Gly)$_3$-Ser (GGGS, SEQ ID NO:9), was included to distance the active sequence from the central framework. Distances between the active sequences can be adjusted by decreasing or increasing the length of the linker, including without limitation by including two linkers in tandem (GGGSGGGS, SEQ ID NO:10), or by inserting any suitable inert linker, including without limitation a polyethylene glycol (PEG) of a variable length. The branched structure was designed to have enhanced activity by causing receptor clustering (cross-linking) on the surface of responsive cells.

The peptides were synthesized on PAL-PEG-polystyrene resin (Applied Biosystems, Foster City, Calif.) utilizing Fmoc (9-fluorenylmethoxycarbonyl)-protected amino acids and a Milligen Biosearch 9050+continuous flow peptide synthesizer (Millipore Corporation, Billerica, Mass.).

The C-terminus of the central framework is typically a lysine (K) residue. However, the C-terminus can be modified to include additional C-terminal amino acids such as a cysteine residue, to which tags such as fluorescent groups can be added, or an ε-biotinyl-N-lysine (biotinyl-K) residue useful for subsequent purification processes. The availability of such sites can therefore be used to advantage in a number of ways, including without limitation to aid in detection, quantification, and purification of the peptides. In addition, an amino acid such as β-alanine (βA) or tryptophan (W) can be inserted between the added C-terminal amino acid and the C-terminal lysine residue of the central framework in order to provide a spacer or a means to determine concentration by absorbance. Non-limiting examples of such modified C-terminal lysine residues on the central framework include K-βA-C and K—W-biotinyl-K, respectively. Furthermore, additional lysine residues can be added to either one or both of the α- and ϵ-amino groups of a modified C-terminal lysine on the central framework to yield, for example, $(K)_2K$, $(K)_2K$-βA-C or $(K)_2K$—W-biotinyl-K, thereby forming branched structures in which the α- and ϵ-amino groups are available for extension.

The lysine residues used at the branch points can be incorporated with Fmoc protection on both the α- and ϵ-amino groups, so that both become available for amide bond formation after the standard deprotection reaction with piperidine. In some embodiments, for example, a suitable fluorescent tag may be incorporated, including without limitation a dansyl group incorporated by reaction with the thiol group on the C-terminal cysteine using 5-((((2-iodoacetyl)amino)ethyl)amino)naphthalene-1-sulfonic acid (1,5-IAEDANS) following a standard protocol for thiol-reactive probes (Invitrogen Corp., Carlsbad, Calif.). Similarly, in these or other embodiments, biotin may be attached to lysine through an amide linkage to the side chain amino group which, because of its high affinity with streptavidin, provides a means to retrieve the peptide with associated proteins from reaction mixtures in order to study the interaction of the peptide with cellular components.

After cleavage from the resin bed, the product can be purified by HPLC on a preparative Jupiter Proteo C12 column (21.2 mm×250 mm) (Phenomenex, Inc., Torrance, Calif.) using a gradient from 8% to 18% acetonitrile in water containing 10 mM trifluoroacetic acid (TFA). The purity of the final peptide product was confirmed by mass spectroscopy performed using a Voyager DE STR mass spectrometer (Applied Biosystems, Foster City, Calif.). HPLC-purified peptide can be dried under vacuum, dissolved in sterile phosphate buffered saline, pH 7.2 (PBS) and passed through a gel filtration column of Sephadex G-15 or G-25 (1×48 cm for small samples) to separate TFA from the peptide. The column may then be eluted with sterile PBS.

Alternatively, the product may be purified by other techniques, including without limitation the use of a $C_{18}$ reverse-phase cartridge, ion exchange chromatography, and gel filtration chromatography to remove side products of synthesis. Concentration can be determined by absorbance of the fluorophore (e.g., dansyl group, extinction coefficient, $\epsilon_{mM}$=5.7 $cm^{-1}$ at 336 nm), absorbance of the peptide bond at 210 nm ($\epsilon_{mg/ml}$≈31 $cm^{-1}$), absorbance of aromatic amino acids (e.g., tryptophan, $\epsilon_{mM}$=5.6 $cm^{-1}$ at 280 nm) in the peptide (when present) and/or absorbance of the bicinchoninic acid reagent (Pierce). The peptide solutions can be adjusted to the desired concentration and filter-sterilized prior to use.

FIGS. 2A-2B illustrate the chemical structures of two embodiments of the present invention that were synthesized and purified according to the methods and procedures outlined above. The peptide constructs illustrated contain four identical sequences, each of which is connected to a branched central tri-lysine framework via a $(Gly)_3$-Ser (GGGS, SEQ ID NO:9) linker sequence. FIG. 2A illustrates a peptide construct 20 according to one embodiment of the present invention, Peptide 6B (SynGia™6B) which contains four copies of the core sequence containing peptide HPSLK (SEQ ID NO:3) 22. The peptide 22 has a molecular mass of 3,685.2 Daltons. FIG. 2B illustrates another type of construct 20 consisting of the construct 20 shown in FIG. 2A, Peptide 6B (SynGia™6B), to which a dansyl tag 25 has been covalently added to the C-terminal β-alanine and cysteine residues. The molecular mass of the dansylated peptide is 4,165.8 Daltons.

FIG. 3 illustrates a Matrix-Assisted Laser Desorption Ionization mass spectrum (MALDI-MS) of the purified Peptide 6B (SynGia™6B) construct 20 whose structure is shown in FIG. 2A. The 3,707 Dalton component is a sodium adduct of the peptide construct which is generated during analysis by mass spectroscopy. The mass spectrum was recorded using a Voyager DE STR mass spectrometer (Applied Biosystems, Foster City, Calif.). Although these data indicate the peptides isolated were essentially pure, substantially or somewhat less purified peptides may also be suitable for use as therapeutic agents.

The peptides illustrated in FIGS. 2A-B are nonlimiting examples of a family of therapeutic peptides according to the present invention which typically have in common one or more of the following properties:

- the ability to act synergistically with antibodies to neutralize HIV;
- the N-terminal amino acid is usually hydrophobic and/or neutral;
- the compositions are rich in proline (P), serine (S), threonine (T) and asparagine (N);
- the order of these amino acids in the sequences is not rigid and can vary;
- a common sequence is XPSX, where X can be any amino acid;
- the sequences vary in length from 4 to 8 amino acids;
- the C-terminal amino acid can vary (e.g., HPSLK (SEQ ID NO:3), HPSLG (SEQ ID NO:4), HPSLL (SEQ ID NO:5), HPSLA (SEQ ID NO:6), etc.); and the internal amino acid sequences can vary (e.g., NPSH-PLSG (SEQ ID NO:7), NPSHPSLG (SEQ ID NO:8), etc.).

Example 2

Synergy Between Antibodies and Peptides

The ability of the peptides to inhibit replication of HIV, both alone and in combination with antibodies, was tested as follows. Approximately 3 million cells of frozen human peripheral blood mononuclear cells (PBMCs), obtained from the California Blood Bank system, are thawed at 37° C. and transferred to a 50 ml conical tube where 8 ml of wash medium are added slowly. Then an additional 8 ml of wash medium are added and swirled to mix. The cells are then centrifuged at 330 g for 10 min, the supernatant is removed and the pellet is resuspended in 10 ml wash medium and centrifuged as above. The washed cells are then resuspended in RPMI-B medium containing 10% FBS, phytohemagglutin is added to 5 µg/ml, and cells are incubated at 37° C. for 24 hr in humidified 5% $CO_2$, Cells are washed, suspended to about 6 million cells per ml, and 50 µl (about 250,000 viable cells) are added to each test well. Then 100 µl of the test peptide is added at a concentration sufficient to provide the desired final concentration, followed by 100 µl of virus suspension (100 median tissue culture infective doses (TCID50s)). The assay plate is incubated 3 days at 37° C., then washed 3 times to remove unbound virus, and the cells are again suspended to 250 µl of medium. After an additional 24 hr of incubation, cells are lysed with Triton X-100 and each sample is assayed by an enzyme-linked immunoassay for virus protein p24 to quantify neutralization of virus. In another set of samples, antibody preparations are also added at a desired concentration (i.e. in addition to peptide).

FIGS. 4A-4D are scatter plots illustrating the inhibition of HIV replication (neutralization) in PBMCs by the peptide construct SynGia™6B (Peptide 6B) containing four copies of the core peptide HPSLK (SEQ ID NO:3) linked to a branched central framework structure (Susavion Biosciences Inc., AZ). Peptide 6B was assayed for activity with two strains of HIV, clade B (Strain SF162) and clade C (Strain 97ZA009), both of which were provided by the California Department of Public Health (Richmond, Calif.). HIV-1 clade B is the major strain in North America and HIV-1 clade C is the major strain in central and southern Africa, India and China. The peptide was assayed either alone (–) or in combination with serum from HIV-infected individuals (+), as outlined below.

| Figure | HIV Strain | Peptide | Serum |
|--------|-----------|---------|-------|
| 4A | clade B | HPSLK (SEQ ID NO: 3) | + |
| 4B | clade B | HPSLK (SEQ ID NO: 3) | – |
| 4C | clade C | HPSLK (SEQ ID NO: 3) | + |
| 4D | clade C | HPSLK (SEQ ID NO: 3) | – |

In the absence of peptide, the antibody preparation (serum) provided only about 30% neutralization at the same dilution (data not shown).

Figure 4A:
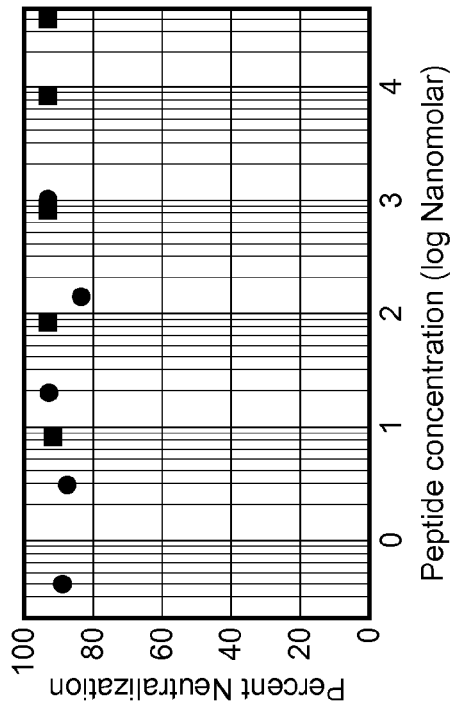
FIG. 4A is a scatter plot illustrating inhibition of HIV-1 clade B replication in human blood cells by one embodiment of the invention, Peptide 6B (SynGia™6B), in the presence of antiserum.
Figure 4B:
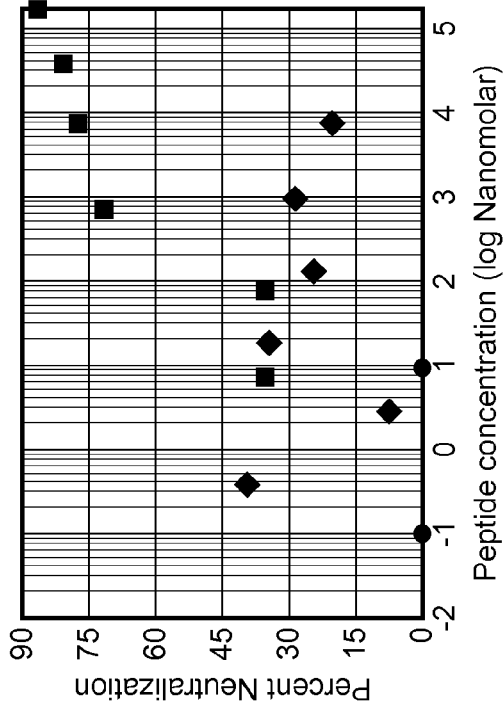
FIG. 4B is a scatter plot illustrating inhibition of HIV-1 clade B replication in human blood cells by one embodiment of the invention, Peptide 6B (SynGia™6B), in the absence of antiserum.
Figure 4C:
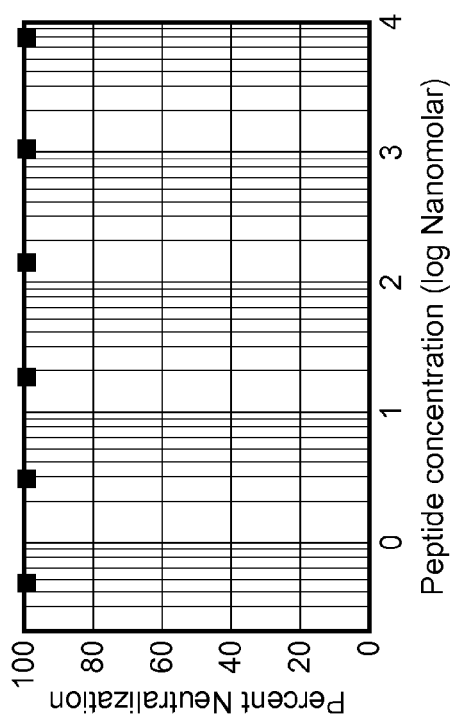
FIG. 4C is a scatter plot illustrating inhibition of HIV-1 clade C replication in human blood cells by one embodiment of the invention, Peptide 6B (SynGia™6B), in the presence of antiserum.
Figure 4D:
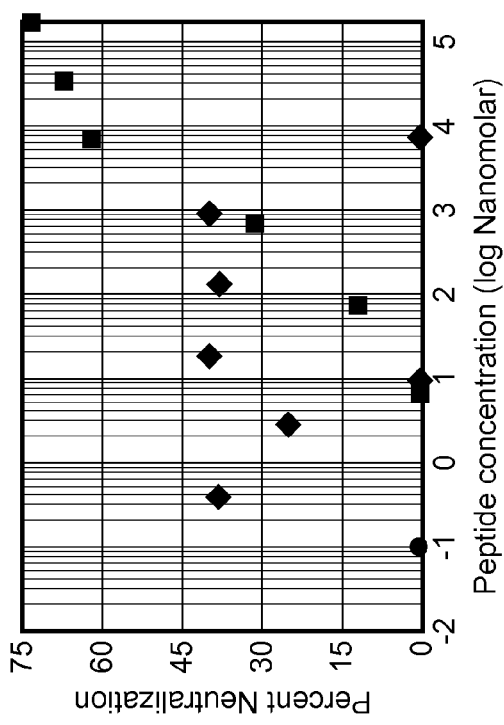
FIG. 4D is a scatter plot illustrating inhibition of HIV-1 clade C replication in human blood cells by one embodiment of the invention, Peptide 6B (SynGia™6B), in the absence of antiserum.

The data shown in FIGS. 4A-4D indicate that the peptides have substantial inhibitory activity when assayed alone. Peptide 6B, the construct containing four copies of the core sequence HPSLK (SEQ ID NO:3), shows particularly strong inhibitory activity at the higher concentrations. However, even at low (picomolar) peptide concentrations, the peptides achieved essentially complete inhibition of viral replication in the presence of antibodies (serum), as shown in FIGS. 4A and 4C. Therefore, the peptides alone at picomolar and nanomolar concentrations achieved inhibition of replication (about 20 to about 40%) and the antibodies alone gave only modest or minimal attenuation of viral replication (about 30%).

In contrast, the peptides achieved nearly quantitative inhibition of viral replication when used in combination with the antibodies, particularly with antibodies from infected individuals. For assays in which antibodies against HIV were combined with the peptides, essentially complete inhibition of replication was achieved. Furthermore, a maximal extent of neutralization was obtained with the lowest concentration of peptide tested, indicating that the peptides are active in the nanomolar concentration range. The antibodies were provided as serum from HIV-infected patients by the California Department of Public Health (Richmond, Calif.) and diluted to a concentration which, in the absence of the peptides (data not shown), provided only about 30% neutralization.

Figure 5A:
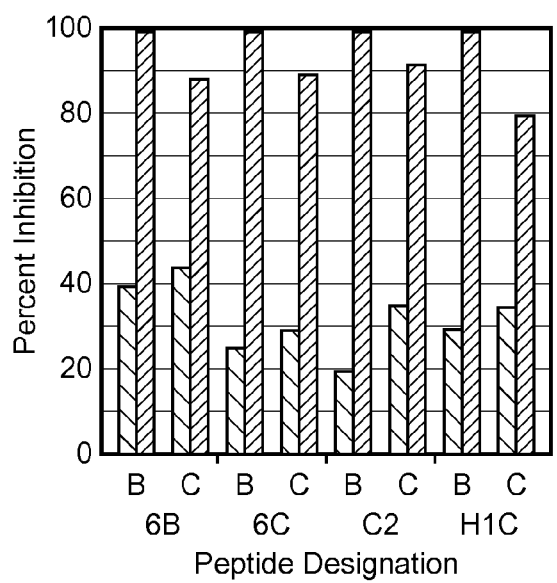
FIG. 5A is a vertical bar graph illustrating the synergistic inhibition of HIV-1 clade B (B) or HIV-1 clade C(C) replication in human blood cells by four peptide embodiments of the invention (Peptides 6B, 6C, C2, and H1C) in either the absence (short bars) or in the presence (long bars) of an antibody preparation which, when assayed alone, provided only about 30% neutralization (Peptide 6B (SynGia™6B) is a construct containing four copies of the core sequence HPSLK (SEQ ID NO:3), Peptide 6C (SynGia™6C) is a construct containing four copies of the core sequence PSSNA (SEQ ID NO:2), Peptide C2 (SynGia™C2) is a construct containing four copies of the core sequence VGGGS (SEQ ID NO:1) and Peptide H1C (SynGia™H1C) is a construct containing four copies of the core sequence NPSHPLSG (SEQ ID NO:7))
Figure 5B:
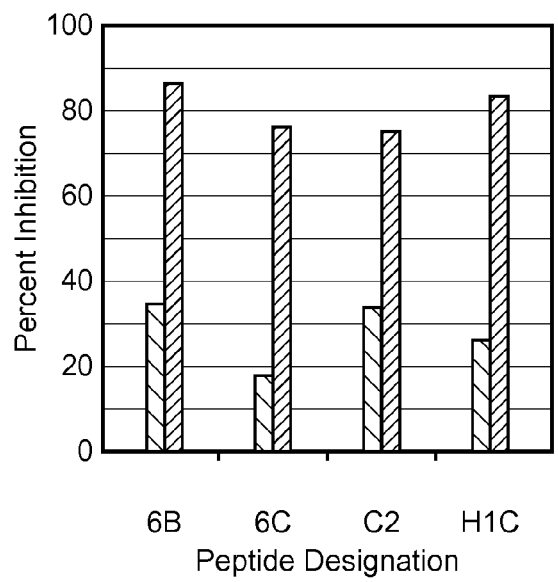
FIG. 5B is a vertical bar graph illustrating the synergistic inhibition of HIV-1 clade C replication in human blood cells by the four embodiments of the invention described in FIG. 5A in both the absence (short bars) or the presence (long bars) of an antibody preparation that, when assayed alone, provided no (about 0%) neutralization.

FIG. 5A and FIG. 5B are vertical bar graphs illustrating the synergistic inhibition of HIV-1 clade B (B) and HIV-1 clade C(C) replication in human blood cells by four different peptide embodiments of the present invention, the constructs Peptide 6B (SynGia™6B) containing four copies of the core sequence HPSLK (SEQ ID NO:3), Peptide 6C (SynGia™6C) containing four copies of the core sequence PSSNA (SEQ ID NO:2), Peptide C2 (SynGia™C2) containing four copies of the core sequence VGGGS (SEQ ID NO:1) and Peptide H1C (SynGia™H1C) containing four copies of the core sequence NPSHPLSG (SEQ ID NO:7) (Susavion Biosciences Inc., AZ). The short bars represent neutralization by peptide alone. The long bars represent neutralization when pooled serum from HIV-positive patients was added along with the peptide. The bars represent averages from two experiments, each performed in quadruplicate. In one set of experiments, each peptide was assayed at 10 nM for the ability to inhibit replication. In the absence of peptide, the antibody preparation (serum) provided only about 30% neutralization (inhibition) at the same dilution (data not shown). The results of this first set of assays is shown in FIG. 5A. In a second set of experiments, peptide was added at 10 nM alone or in the presence of an anti-HIV-1 antibody preparation (gifted by Dr. Tsafrir Mor, The Biodesign Institute at Arizona State University, Tempe, Ariz.) which, in the absence of peptide, provided no neutralization (data not shown). The results of this second set of assays is shown in FIG. 5B. The data shown in FIGS. 5A and 5B indicate that all four peptides displayed substantial inhibitory activity when assayed alone, that the level of inhibition was enhanced by adding antibodies, and that Peptide 6B containing four copies of HPSLK, (SEQ ID NO:3) displayed the strongest inhibition of the four peptides assayed.

The data shown in FIGS. 4A-D and FIGS. 5A-B indicate that the peptides acted synergistically with the antibodies in the serum. Synergy between the peptides and antibodies is dramatically demonstrated in FIG. 5B, which illustrates results of an assay with a peptide added alone (short bars) or in combination with an antibody preparation that itself provided no neutralization (long bars). In combination with the peptide, 80% to 90% inhibition of replication was achieved.

In another experiment, the addition of a peptide to cultures of a T cell line (MT2) inhibited HIV replication from 10% to 25%, depending on the peptide. Addition of antiserum in these experiments did not show a synergistic effect (data not shown).

Therefore, the synergy demonstrated in FIGS. 4A-D and FIGS. 5A-B indicates a role of the peptide that can be separate from it potential action on lymphocytes. Clearly, the effect of the peptides can be more than a simple additive effect of the peptide plus antibodies, and very likely results from activation of phagocytes. Without such activation, one would not expect the virus-antibody complex to be effectively cleared via Fc-mediated phagocytosis by these cells.

Example 3

Induction of Cytokine Release

To determine whether inhibition of HIV replication by the peptide may be the result of induction of release of cytokines, cultured PBMCs were treated with one peptide embodiment of the present invention and, after 4 hour incubation, the medium was collected and assayed for changes in the amounts of 40 different cytokines. The HPSLK (SEQ ID NO:3) peptide construct 28 shown in FIG. 2B was added at a concentration of 100 nM in each of the assays. The PBMC cultures were established as described in Example 1 with cells from Cellular Technologies, Ltd. (Shaker Heights, Ohio). Approximately 3 million cells of frozen human PBMCs are thawed at 37° C. and transferred to a 50 ml conical tube where 8 ml of wash medium are added slowly. Then an additional 8 ml of wash medium are added and swirled to mix. The cells are then centrifuged at 330 g for 10 min, the supernatant is removed and the pellet is resuspended in 10 ml wash medium and centrifuged as above. The washed cells are then resuspended in RPMI-1640 medium containing 10% FBS to about 6 million cells per ml and 100 µl of the suspension are added into each well of a 96-well microtiter plate and incubated overnight at 37° C. in humidified 5% $CO_2$. After 24 hr the medium is replaced with 200 µl fresh RPMI-1640 medium containing 10% FBS and incubated at 37° C. in humidified 5% $CO_2$ for 2 days. For the data shown in Table 1, the peptide aliquot was then added to samples in duplicate at a final concentration of 100 nM and incubated at 37° C. in humidified 5% $CO_2$ for 4 hr. For other experiments (data not included), the incubation was continued for 24 hr. The medium is then removed and stored at −80° C. The samples are analyzed for production of cytokines. One set of control cells is not treated with an experimental agent. A second set of control cells is treated with LPS, an agent commonly used to induce production of a variety of inflammatory cytokines. The positive control for inflammation is essential to ensure that the peptides do not produce an unregulated inflammatory response.

Culture medium is removed for assay of cytokine levels with methods developed by RayBiotech, Inc. (Norcross, Ga.). In this technology, membrane arrays of antibodies against cytokines are incubated with samples of media. After washing, the array is incubated with a cocktail of all antibodies tagged with biotin. The membrane is then washed free of unbound antibodies and incubated with streptavidin labeled with a fluorescent dye. After a final wash, the membrane arrays are read in a fluorescence detector.

The peptides did not cause cytotoxicity, as assayed by a double-dye method in which acridine orange fluoresces green in viable cells and ethidium bromide fluoresces red in dead cells. Toxicity of the peptide in vivo is tested by injection of a peptide into animals. The peptides can be administered in a number of ways, including without limitation by injection (intravenously, subcutaneously, intramuscularly or intraperitoneally, topically (transmucosally, transbuccally, or transdermally) and/or orally (liquid, tablet or capsule). In preliminary studies on mice, no adverse effects of the peptide have been observed (data not shown). In contrast, treated animals appear to exhibit enhanced well being, which might be a beneficial side effect of enhanced immunity in otherwise healthy subjects.

Table 1 contains data showing cytokines that are released at a significantly higher rate during a 4-hour incubation of PBMCs with the branched peptide construct 28 in the presence of serum; that construct 28, whose structure is illustrated in FIG. 2B, contained the core peptide sequence HPSLK (SEQ ID NO:3) (SynGia™6B). Among these cytokines are IL-2, IL-4, IL-16, IL-17, TNF-β and TIMP-2. Several cytokines, in particular IL-16, IL-17, TNF-β and TIMP-2 show more than a two-fold increase over untreated control samples.

TABLE 1

Relative Cytokine Concentration after Incubation of PBMCs in Serum with Peptide Construct SynGia ™6B Containing the Core Sequence HPSLK (SEQ ID NO: 3).

| Cytokine | HPSLK (SEQ ID NO: 3) | Untreated | LPS |
|---|---|---|---|
| Increased: | | | |
| Eotaxin-2 | 562 | 194 | 221 |
| ICAM-1 | 87 | 57 | 53 |
| I-309 | 101 | 26 | 39 |
| IL-2 | 131 | 86 | 80 |
| IL-3 | 168 | 130 | 132 |
| IL-4 | 64 | 30 | 49 |
| IL-6 | 202 | 98 | 4375 |
| IL-16 | 10 | 1 | 2 |
| IL-17 | 27 | 5 | 11 |
| TNF-β | 117 | 38 | 95 |
| TIMP-2 | 230 | 58 | 92 |
| sTNF RI | 83 | 42 | 58 |
| sTNF RII | 30 | 9 | 27 |
| Decreased: | | | |
| IL-1a | 169 | 225 | 246 |
| IL-13 | 105 | 138 | 126 |
| IL-11 | 0 | 17 | 27 |
| IL-12p40 | 17 | 108 | 46 |
| IL-12p70 | 32 | 90 | 89 |

As shown in the example in Table 1, the peptide stimulated release of several important cytokine. IL-2 activates T, B and natural killer cells and is used therapeutically. IL-4 promotes proliferation and differentiation of B-cells and inhibits production of inflammatory cytokines such as IL-1, IL-6 and TNF-α and should attenuate secretion of TNF-α as treatment continues. Furthermore, the stimulation of secretion of sTNF RI and sTNF RII, soluble forms of the receptor for TNF-α, an inflammatory cytokine, should mitigate its deleterious effects. Thus, an inflammatory response to treatment with the peptide may occur but be transient. Stimulation of release of highly inflammatory cytokines, such as IL-1 and IL-6, was minimal. For example, in the experiment shown in Table 1, release of IL-6 was 202 (arbitrary units) in the experimental sample, 98 in the untreated sample, but 4,375 in the LPS-treated sample. IL-16 is secreted by CD8(+) cells (lymphocytes), is a natural ligand for CD4, and suppresses replication of HIV. IL-17 is produced by activated CD4(+) T cells, enhances expression of ICAM-1, IL-6, IL-8 and G-CSF, and is a mediator of angiogenesis.

Of particular importance, the peptide did not stimulate release of IL-10, a cytokine correlated with suppression of the TH1 immune system in HIV-infected individuals.

This pattern of cytokine release, with the indication of macrophage activation, provides real promise that the peptides of the present invention will be particularly well suited to treatment of HIV infections and other infectious diseases.

In other embodiments of the invention, release of other beneficial cytokines such as IL-8 and IL-15 by PBMCs can be stimulated. In one embodiment, for example, the cytokines IL-8, IL-15, IL-16, RANTES or combinations thereof may be stimulated.

Therefore, the mixture of cytokines released from PBMCs in response to the peptides described herein should provide, either in isolation or in combination with other treatments, an effect therapy against HIV infections. Treatment with the peptides of the present invention should induce activation of cells of the immune system in vivo and provide a sustained endogenous elevation of beneficial cytokines, in contrast to the rapid disappearance of these proteins when given exogenously. In addition, the peptides of the present invention can also stimulate release of TNF-α, a marker of TH2-type macrophage activation. Although IL-8 and TNF-α are inflammatory, their secretion is a normal function of monocyte/macrophage activity and can be calibrated by the amount of peptide administered.

Another important application of the present invention may be the use of the peptides as microbicides, which are preparations that can be formulated for transmucosal delivery, including without limitation gels, creams, films, or suppositories that can be applied in various combinations inside the vagina or rectum to protect against sexually transmitted infections including HIV. Microbial infections suitable for treatment according to the invention include without limitation bacterial, viral, protozoal, and fungal infections.

In addition to its therapeutic potential for treatment, the technology of the present invention can be used for other applications, including application as a preliminary in vitro test prior to therapy. The immune system of a HIV-infected person is apparently incapable of maintaining a long-term defense against the infection. The causes of viral escape from the immune system could be (1) the result of mutations in the viral genome which render the virus epitope-free and thus not subject to binding by an antibody, or (2) the phagocytic cells that are responsible for eliminating the virus-antibody complex are quiescent. To discriminate between these possibilities, samples of blood from an individual infected with a virus such as HIV could be incubated with and without addition of a peptide of the present invention. In the former case, the synergistic activity of the peptides would not be achieved when viral epitopes to which antibodies bind are not present. However, in the latter case, the peptides could activate phagocytes and achieve elimination of the virus. Either way, the results would then be available to allow the decision of whether to proceed to treatment, and the results described in this document demonstrate the feasibility of this test.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. Although the examples herein disclose the therapeutic efficacy of the peptides of the present invention with respect to neutralizing replication of the HIV virus, for example, the peptides should also be useful to diagnose or treat a wide variety of infections or disorders, including prophylactic treatments for prevention of such maladies, and for enhancing or stabilizing the well being of healthy subjects. Furthermore, larger peptides containing active core sequences could potentially enhance the therapeutic benefits disclosed herein.

We claim:

1. A therapeutic peptide consisting of a construct and at least two arms, the construct having a central framework and each arm consisting of a core sequence linked to the central framework via a linker sequence, wherein each core sequence is the same or different and is selected from the group consisting of: VGGGS (SEQ ID NO: 1), PSSNA (SEQ TD NO:2), HPSLK (SEQ TD NO:3), HPSLG (SEQ TD NO:4), HPSLL (SEQ ID NO:5), HPSLA (SEQ TD NO:6), NPSHPLSG (SEQ TD NO:7), and NPSHPSLG (SEQ ID NO:8).

2. The therapeutic peptide of claim 1, wherein the central framework is a tri-lysine framework and the linker sequence is GGGS (SEQ TD NO:9).

3. The therapeutic peptide of claim 1, wherein the core sequence is PSSNA (SEQ TD NO:2), the linker sequence is GGGS (SEQ TD NO:9), and the therapeutic peptide is branched having four core sequences each being PSSNA (SEQ TD NO:2).

4. An immunostimulatory composition comprising the therapeutic peptide of claim 1.

5. The composition of claim 4, wherein the therapeutic peptide comprises three or four arms that are the same.

6. The composition of claim 5, wherein the linker sequence is GGGS (SEQ TD NO:9) and the construct is branched.

7. A treatment method comprising administering an effective dose of the composition of claim 4 to a subject for treating at least one medical condition, the condition comprising at least one of a microbial infection, a cell proliferative disease and an immunosuppressive disorder, wherein the composition is administered in an amount sufficient to regulate the release of a specific pattern of cytokine molecules in the subject and stimulates the immune system of the subject.

8. The method of claim 7, wherein administering the composition stimulates:

the production of at least one therapeutically beneficial cytokine; and the activity of at least one pathogen-directed antibody.

9. A diagnostic method of evaluating the capacity of an immune system to respond to at least one pathogen-directed antibody and/or to neutralize replication of a virus or excessive cell proliferation comprising:

incubating at least one portion of at least one test sample in the presence of at least one composition according to claim 4; and optionally, incubating at least one portion of the at least one test sample in the absence of at least one composition according to claim 4, thereby providing a control.

10. The diagnostic method of claim 9, wherein the virus is a human immunodeficiency virus.

11. A therapeutic peptide consisting of an amino acid sequence selected from the group consisting of VGGGS (SEQ ID NO:1), PSSNA (SEQ TD NO:2), HPSLK (SEQ TD NO:3), HPSLG (SEQ ID NO:4), HPSLL (SEQ TD NO:5), HPSLA (SEQ TD NO:6), NPSHPLSG (SEQ ID NO:7), and NPSHPSLG (SEQ TD NO:8).

12. The therapeutic peptide of claim 11, wherein the peptide is VGGGS (SEQ TD NO:1).

13. The therapeutic peptide of claim 11, wherein the peptide is PSSNA (SEQ TD NO:2).

14. The therapeutic peptide of claim 11, wherein the peptide is HPSLK (SEQ ID NO:3).

15. The therapeutic peptide of claim 11, wherein the peptide is NPSHPLSG (SEQ ID NO:7).

16. The therapeutic peptide of claim 11, wherein the peptide is NPSHPSLG (SEQ ID NO:8).

17. The method of claim 7, wherein the viral infection is human immunodeficiency virus and/or the cell proliferative disease is cancer.

18. The diagnostic method of claim 7, wherein the virus is human immunodeficiency virus and/or the excessive cell proliferation is related to cancer.

19. A therapeutic branched peptide consisting of a tri-lysine core and four peptides, each peptide consisting of the sequence PSSNA (SEQ TD NO:2) linked to the tri-lysine core via a linker sequence consisting of GGGS (SEQ TD NO:9).

20. The therapeutic peptide of claim 1, wherein the core sequence is VGGGS (SEQ TD NO:1).

21. The therapeutic peptide of claim 1, wherein the core sequence is PSSNA (SEQ TD NO:2).

22. The therapeutic peptide of claim 1, wherein the core sequence is HPSLK (SEQ ID NO:3).

23. The therapeutic peptide of claim 1, wherein the core sequence is NPSHPLSG (SEQ ID NO:7).

24. The therapeutic peptide of claim 1, wherein the core sequence is NPSHPSLG (SEQ ID NO:8).

25. The therapeutic peptide of claim 1, wherein the core sequence is HPSLL (SEQ TD NO:5).

26. A therapeutic peptide comprising an amino acid sequence selected from the group consisting of NPSHPLSG (SEQ ID NO:7) and NPSHPSLG (SEQ ID NO:8).

* * * * *

SEQUENCE LISTING

<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 1

Val Gly Gly Gly Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 2

Pro Ser Ser Asn Ala
1               5

<210> SEQ ID NO 3
<211> LENGTH: 5
<212> TYPE: PRT

```
<213> ORGANISM: Artificial Sequence
<220> FEATURE:
<223> OTHER INFORMATION: Synthetic Sequence

<400> SEQUENCE: 3

His Pro Ser Leu Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 4

His Pro Ser Leu Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Syntthetic Sequence

<400> SEQUENCE: 5

His Pro Ser Leu Leu
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 6

His Pro Ser Leu Ala
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 7

Asn Pro Ser His Pro Leu Ser Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 8

Asn Pro Ser His Pro Ser Leu Gly
1               5

<210> SEQ ID NO 9
<211> LENGTH: 4
<212> TYPE: PRT
<213> ORGANISM: Artificial Sequence
```

```
-continued

<220> FEATURE:
<223> OTHER INFORMATION: linker sequence

<400> SEQUENCE: 9

Gly Gly Gly Ser
1

<210> SEQ ID NO 10
<211> LENGTH: 8
<212> TYPE: PRT
<213> ORGANISM: Artificial Sequence
<220> FEATURE:
<223> OTHER INFORMATION: linker sequence

<400> SEQUENCE: 10

Gly Gly Gly Ser Gly Gly Gly Ser
1               5
```